United States Patent [19]

Siegel et al.

[11] Patent Number: 5,380,941
[45] Date of Patent: Jan. 10, 1995

[54] PREPARATION OF AROMATIC UREAS WHICH CONTAIN A THIOETHER OR SULFONYL GROUP

[75] Inventors: Bernd Siegel, Ludwigshafen; Manfred Patsch, Wachenheim, both of Germany

[73] Assignee: BASF Aktiengesellschaft, Ludwigshafen, Germany

[21] Appl. No.: 130,176

[22] Filed: Oct. 1, 1993

[30] Foreign Application Priority Data

Oct. 1, 1992 [DE] Germany .................... 4233033

[51] Int. Cl.$^6$ .................... C07C 275/28; C07C 273/18
[52] U.S. Cl. .................... 564/48; 544/390; 558/413; 558/417; 560/9; 560/12; 560/251; 562/426; 562/430; 562/432; 564/50; 564/52; 564/53; 564/54; 564/55
[58] Field of Search .................... 564/48, 50, 52, 53, 564/54, 55; 558/413, 417; 544/390; 560/9, 12, 251; 562/426, 430, 432

[56] References Cited

U.S. PATENT DOCUMENTS

| | | |
|---|---|---|
| 4,841,028 | 6/1989 | Aeschlimann et al. . |
| 5,091,016 | 2/1992 | Krajicek et al. . |
| 5,283,362 | 2/1994 | Hackl et al. . |

FOREIGN PATENT DOCUMENTS

| | | |
|---|---|---|
| 0503385 | 9/1962 | European Pat. Off. . |
| 0515844 | 12/1992 | European Pat. Off. . |
| 0531689 | 3/1993 | European Pat. Off. . |
| 2256275 | 5/1973 | Germany . |

OTHER PUBLICATIONS

Japanese Patent 24 900/69 (Abstract only) Oct. 21, 1969.
Houben-Weyl Methoden der Organischen Chemie vol. 9, pp. 135-138 (1958).
Houben-Weyl "Methoden der Organischen Chemie" vol. 8, pp. 149-163 (1952).

*Primary Examiner*—Peter O'Sullivan
*Attorney, Agent, or Firm*—Oblon, Spivak, McClelland, Maier & Neustadt

[57] ABSTRACT

A process for preparing ureas of the formula

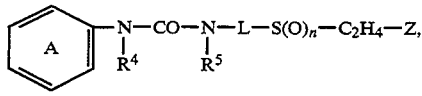

where
the ring A can be substituted and benzo-fused and
n is 0 or 2,
$R^4$ and $R^5$ are hydrogen, $C_1$–$C_4$-alkyl or phenyl,
L is unsubstituted or substituted $C_2$–$C_4$-alkylene, or $NR^5$ and L are together the radical of the formula

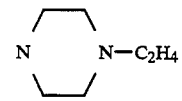

and
Z is hydroxyl or a radical which can be eliminated under alkaline reaction conditions,
by reacting a phenylurea of the formula

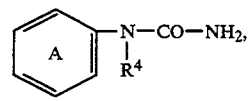

where $R^4$ and the ring A each have the abovementioned meanings, with an amine of the formula

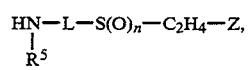

where n, $R^5$, L and Z each have the abovementioned meanings, at from 80° to 180° C. in the presence or absence of an inert diluent is described.

6 Claims, No Drawings

PREPARATION OF AROMATIC UREAS WHICH CONTAIN A THIOETHER OR SULFONYL GROUP

The present invention relates to a novel process for preparing N-phenyl- or N-naphthyl-ureas which have a thioether or sulfonyl group in the molecule, in which an unsubstituted N-phenyl- or N-napnthylurea is made to react with an amine which contains a thioether or sulfonyl group in the molecule.

Aromatic ureas which contain a thioether or sulfonyl group are described in U.S. Pat. No. 5,091,516. However, their preparation is complicated since it proceeds via aromatic isocyanates.

It is an object of the present invention to make available a novel process for preparing aromatic ureas which contain a thioether or sulfonyl group in the molecule. The novel process should be easy to carry out and should give the end products in good yield and high purity. The starting materials used should additionally be easily accessible.

We have found that this object is achieved in that the preparation of ureas of the formula I

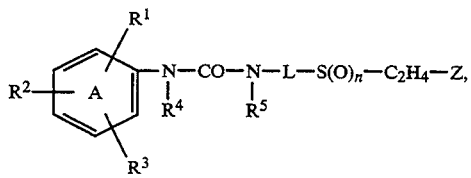

where n is 0 or 2, $R^1$, $R^2$ and $R^3$ independently of one another are each hydrogen, $C_1$–$C_4$-alkyl, $C_1$–$C_4$-alkoxy, halogen, hydroxyl, hydroxysulfonyl, carboxyl, cyano, nitro, $C_2$–$C_4$-alkanoylamino or $C_1$–$C_4$-alkoxycarbonylamino, $R^4$ and $R^5$ independently of one another are each hydrogen, $C_1$–$C_4$-alkyl or phenyl, L is $C_2$–$C_4$-alkylene which may be interrupted once by oxygen, imino or N—($C_1$–$C_4$-alkyl)imino, or $NR^5$ and L together are the radical of the formula

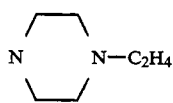

and

Z is hydroxyl or a group which can be eliminated under alkaline reaction conditions and the ring A can be benzo-fused, takes place advantageously when a phenylurea of the formula II

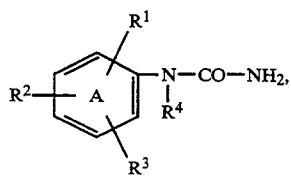

where $R^1$, $R^2$, $R^3$, $R^4$ and the ring A each have the abovementioned meanings, is reacted with an amine of the formula III

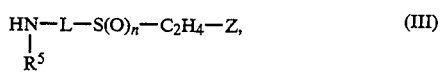

where n, $R^5$, L and Z each have the abovementioned meanings, at from 80° to 180° C., in the presence or absence of an inert diluent.

All alkyl and alkylene groups appearing in the abovementioned formulae can be either straight-chain or branched.

The radicals $R^1$, $R^2$, $R^3$, $R^4$ and $R^5$ are, e.g. methyl, ethyl, propyl, isopropyl, butyl, isobutyl or sec-butyl.

The radicals $R^1$, $R^2$ and $R^3$ are furthermore, e.g. methoxy, ethoxy, propoxy, isopropoxy, butoxy, isobutoxy, sec-butoxy, fluorine, chlorine, bromine, acetylamino, propionylamino, butyrylamino, isobutyrylamino, methoxycarbonylamino, ethoxycarbonylamino, propoxycarbonylamino, isopropoxycarbonylamino or butoxycarbonylamino.

The radicals L are, e.g. ethylene, 1,2- or 1,3-propylene, 1,2-, 1,3-, 1,4- or 2,3-butylene, 3-oxa-1,4-butylene, 3-aza-1,4-butylene, 3-aza-3-methyl-1,4-butylene or 3-aza-3-ethyl-1,4-butylene.

The radical Z is, inter alia, a group which can be eliminated under alkaline reaction conditions. Groups of this type are, e.g. chlorine, bromine, $C_1$–$C_4$-alkylsulfonyl, phenylsulfonyl, $OSO_3H$, $SSO_3H$, $OP(O)(OH)_2$, $C_1$–$C_4$-alkylsulfonyloxy, unsubstituted or substituted phenylsulfonyloxy, $C_1$–$C_4$-alkanoyloxy, $C_1$–$C_4$-dialkylamino or a radical of the formula

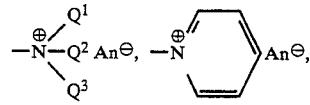

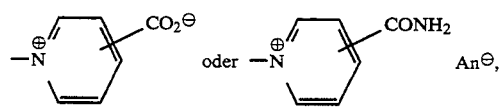

where $Q^1$, $Q^2$ and $Q^3$ independently of one another in each case have the meaning of $C_1$–$C_4$-alkyl or benzyl and $An^\ominus$ in each case has the meaning of one equivalent of an anion. Suitable anions here are, e.g. fluoride, chloride, bromide, iodide, mono-, di- or trichloroacetate, methanesulfonate, benzenesulfonate or 2- or 4-toluenesulfonate.

Suitable inert diluents which can be used in the process according to the invention are, e.g. water or organic solvents, such as toluene, xylene, nitrobenzene, chlorobenzene, dichlorobenzene, N,N-dimethylformamide, N,N-dimethylacetamide or N-methylpyrrolidinone.

The novel process is carried out at 80°–180° C., preferably 95°–150° C., the process as a rule being carried out under atmospheric pressure.

In general, from 1 to 1.5 mol, preferably from 1 to 1.2 mol, of amine of the formula III can be used per mole of phenylurea of the formula II.

A procedure is preferred in which the reaction is carried out in the presence of an inert diluent. In this case, usually from 100 to 500% by weight, preferably from 150 to 300% by weight, of diluent are used, in each case based on the weight of phenylurea II.

Particularly suitable diluents are, e.g. toluene, xylene or N,N-dimethylacetamide.

A process for preparing ureas of the formula I in which the ring A is not benzo-fused is preferred.

A process for preparing ureas of the formula I in which $R^3$ is hydrogen is furthermore preferred.

A process for preparing ureas of the formula I in which $R^1$ is nitro, acetylamino or methoxycarbonylamino and $R^2$ is hydrogen, $C_1$–$C_4$-alkyl, $C_1$–$C_4$-alkoxy, chlorine, hydroxysulfonyl or carboxyl is furthermore preferred.

A process for preparing ureas of the formula I in which $R^4$ is hydrogen and $R^5$ is hydrogen or methyl is furthermore preferred.

A process for preparing ureas of the formula I in which L is $C_2$–$C_4$-alkylene which may be interrupted once by oxygen is furthermore preferred.

A process for preparing ureas of the formula I in which Z is hydroxyl is furthermore preferred.

A procedure for preparing ureas of the formula Ia

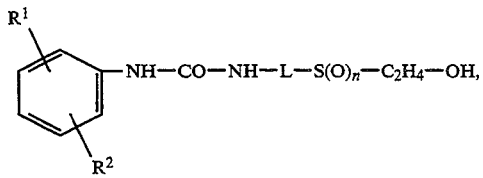

where n is 0 or 2, $R^1$ is nitro or acetylamino, $R^2$ is hydrogen, methyl, methoxy, chlorine, hydroxysulfonyl or carboxyl and L is $C_2$–$C_4$-alkylene which may be interrupted once by oxygen, is to be emphasized, in which a phenylurea of the formula IIa

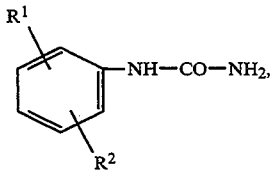

where $R^1$ and $R^2$ each have the abovementioned meanings, is reacted with an amine of the formula IIIa

in which n and L each have the abovementioned meanings.

The process according to the invention is expediently carried out by initially introducing the phenylurea II, amine III and, if appropriate, the inert diluent and heating to the temperature according to the invention with stirring.

After a reaction time which as a rule is 2 to 40 hours, the reaction mixture is cooled and worked up by methods known per se. For example, the diluent which may be present can be removed by distillation or else, if it is an organic, water-miscible diluent, the reaction mixture can be diluted with water, and the end product which is obtained as a precipitate can be separated off and, if appropriate, washed and dried.

Depending on the meanings of n and Z, various preparation variants can be carried out. For example, an amine III which contains a thioether group can be made to react with the phenylurea II and, if appropriate, an oxidation to the sulfonyl group then performed, z.B. with hydrogen peroxide. However, it is also possible to react an amine III, which already contains a sulfonyl group in the molecule, with the phenylurea II.

An amine III which has a hydroxyethyl group can additionally be made to react and, if appropriate, the group which can be removed under alkaline reaction conditions then introduced. However, it is also possible to react an amine III which already contains a group which can be removed under alkaline reaction conditions in the molecule, directly with the phenylurea II. In both cases, as mentioned above, the amine III can have either a thioether or a sulfonyl group.

The phenylureas of the formula II and the amines of the formula III are in general compounds which are known per se. Phenylureas of the formula II are known, e.g. from Houben-Weyl "Methoden der Organischen Chemie" (Methods of Organic Chemistry), Volume 8, pages 149 to 163, or can be obtained by the methods described there. Amines of the formula III are described, e.g. in JP-A-24900/1969 or can be obtained, e.g. from ethyleneimine and 2-mercaptoethanol by methods known per se, as mentioned in Houben-Weyl "Methoden der Organischen Chemie" (Methods of Organic Chemistry), Volume 9, page 135.

By means of the process according to the invention, which can be carried out either continuously or batchwise, the end products are obtained in a simple manner and in good yield and high purity.

The ureas of the formula I obtainable by means of the process according to the invention are useful intermediates for preparing reactive dyes, such as are described, for example, in U.S. Pat. Nos. 4,841,028, 5,091,516, EP-A-503,385 or in the earlier Patent Application EP-A-515,844.

The examples illustrate the invention.

EXAMPLE 1 a) 770 g of a water-moist suction filter cake (dry matter content: 47% by weight) of 3-nitrophenylurea were treated with 860 g of xylene (isomer mixture) and 290.4 g of 2-aminoethyl-2'-hydroxyethyl sulfide and the mixture was heated to boiling. The xylene/water azeotrope boiling at 95° C. was removed by distillation and the reaction mixture was then heated to 140° C. to remove the residual xylene. After completion of the reaction (TLC checking), 495 g of the compound of the formula

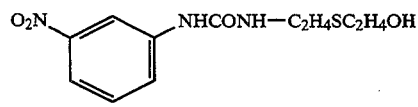

remained.

1H NMR (d6 DMSO): δ=2.55 (m, 4H, CH$_2$—S—CH$_2$); 3.30 (q, 2H, CH$_2$); 3.53 (q, 2H, CH$_2$); 4.82 (bs, 1H, OH); 6.50 (t, 1H, NH); 7.50–7.75 (m, 3H, aromatic H); 8.53 (s, 1H, aromatic H); 9.22 (s, 1H, NH) ppm.

b) 542 g of the compound described in a) were treated with 2 g of tungstic acid and 1600 ml of water (temp.: 80° C.) and oxidized at from 90° to 95° C. using 565 g of 30% strength by weight aqueous hydrogen peroxide.

After completion of the peroxide addition, the reaction mixture was temperature-controlled at 90° C. until it crystallized. It was then cooled to room temperature and the resulting precipitate was filtered off with suction. 586 g of a yellow solid of the formula

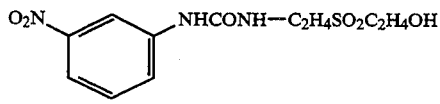

remained.

The compounds shown in the following table are obtained in a similar manner to Example 1.

TABLE

| Ex. No. | Compound |
|---|---|
| 2 | O$_2$N—C$_6$H$_4$—NHCONH—C$_3$H$_6$SO$_2$C$_2$H$_4$OH |
| 3 | O$_2$N—C$_6$H$_4$—NHCON(CH$_3$)—C$_2$H$_4$SO$_2$C$_2$H$_4$OH |
| 4 | O$_2$N—C$_6$H$_4$—NHCONH—C$_2$H$_4$—O—C$_2$H$_4$—SO$_2$C$_2$H$_4$OH |
| 5 | O$_2$N—C$_6$H$_4$—NHCON(piperazine)N—C$_2$H$_4$SO$_2$C$_2$H$_4$OH |
| 6 | 4-Cl-3-O$_2$N-C$_6$H$_3$—NHCONH—C$_2$H$_4$SO$_2$C$_2$H$_4$OH |
| 7 | 4-CH$_3$-3-O$_2$N-C$_6$H$_3$—NHCONHH—C$_2$H$_4$SO$_2$C$_2$H$_4$OH |
| 8 | 4-CH$_3$O-3-O$_2$N-C$_6$H$_3$—NHCONH—C$_2$H$_4$SO$_2$C$_2$H$_4$OH |
| 9 | 3-HO$_3$S-2-NO$_2$-C$_6$H$_3$—NHCONH—C$_2$H$_4$SO$_2$C$_2$H$_4$OH |
| 10 | 2-CO$_2$H-4-NO$_2$-C$_6$H$_3$—NHCONH—C$_2$H$_4$SO$_2$C$_2$H$_4$OH |
| 11 | 1-OH-3-HO$_3$S-6-(N(CH$_3$))CONH—C$_2$H$_4$SO$_2$C$_2$H$_4$OH-naphthalene |
| 12 | 1-OH-3-HO$_3$S-6-NHCONH—C$_2$H$_4$SO$_2$C$_2$H$_4$OH-naphthalene |
| 13 | 3-CH$_3$CO-C$_6$H$_4$—NHCONH—C$_2$H$_4$SO$_2$C$_2$H$_4$OH |
| 14 | 3-CH$_3$COHN-C$_6$H$_4$—NHCONH—C$_2$H$_4$SO$_2$C$_2$H$_4$OH |

EXAMPLE 15

121 g of 2-Aminoethyl-2'-hydroxyethyl sulfide and 1.0 g of sodium tungstate×2H$_2$O were added to a mixture of 500 g of ice and 56.3 g of conc. sulfuric acid and the mixture was warmed to 80° C. The thioether was oxidized to the sulfone at the above temperature using 227 g of 30% strength by weight aqueous hydrogen peroxide. After completion of the reaction, the reaction mixture was cooled to room temperature, adjusted to a pH of 7 using 25% strength by weight sodium hydroxide solution and treated with 385 g of water-moist suction filter cake (dry matter content: 44% by weight) of 3-nitrophenylurea. After addition of 300 ml of N,N-dimethylacetamide, the reaction mixture was heated to boiling and the water was removed to the greatest possible extent by distillation. To complete the reaction, the reaction mixture was subsequently temperature-controlled at 140° C. for a further 4 hours. After completion of the reaction, the mixture was cooled to room temperature and the reaction product was precipitated by addition of 1500 ml of water, filtered off with suction, washed and dried. 195 g of the compound described in Example 1b remained.

The compounds shown in the table are also obtainable by the route described in Example 15.

EXAMPLE 16

285 g of the compound of the formula

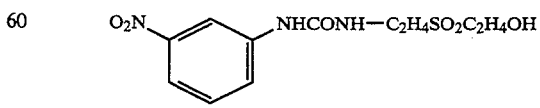

were heated to 95° C. with 408 g of acetic anhydride. After reaction was complete (TLC checking), the excess acylating agent was decomposed with water and the resulting precipitate was filtered off with suction at room temperature. 323 g of the compound of the formula

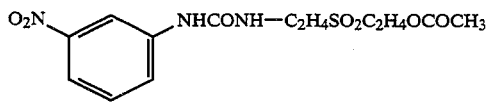

were obtained. Melting point: 161°–163° C.

The following derivatives can be prepared in a similar manner:

| Ex. No. | Compound |
|---|---|
| 17 | 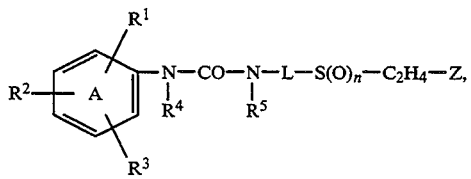 |
| 18 | |

We claim:

1. A process for preparing a urea of the formula I $$\text{(I)}$$

where
   n is 0 or 2,
   $R^1$, $R^2$ and $R^3$ independently of one another are each hydrogen, $C_1$–$C_4$-alkyl, $C_1$–$C_4$-alkoxy, halogen, hydroxyl, hydroxysulfonyl, carboxyl, cyano, nitro, $C_2$–$C_4$-alkanoylamino or $C_1$–$C_4$-alkoxycarbonylamino, $R^4$ and $R^5$ independently of one another are each hydrogen, $C_1$–$C_4$-alkyl or phenyl,
   L is $C_2$–$C_4$-alkylene which may be interrupted once by oxygen, imino or N—($C_1$–$C_4$-alkyl)imino, or $NR^5$ and L together are the radical of the formula

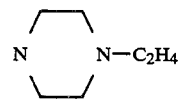

and
   Z is hydroxyl or a group which is eliminated under alkaline reaction conditions and where ring A is optionally benzo-fused, which comprises: reacting a phenylurea of the formula II

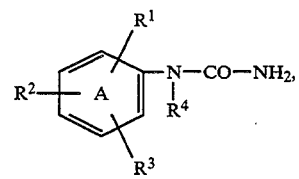 (II)

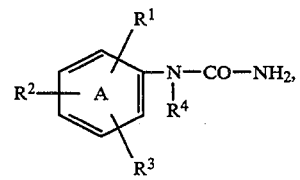 (II)

where $R^1$, $R^2$, $R^3$, $R^4$ and the ring A each have the abovementioned meanings, with an amine of the formula III

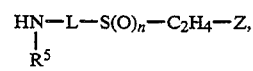 (III)

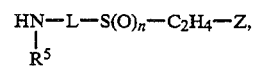 (III)

where n, $R^5$, L and Z each have the abovementioned meanings, at from 80° to 180° C., in the presence or absence of an inert diluent.

2. The process of claim 1, wherein the reaction is conducted in the presence of an inert diluent.

3. The process of claim 2 wherein said diluent is toluene, xylene, nitrobenzene, chlorobenzene, dichlorobenzene, N,N-dimethylformamide, N,N-dimethylacetamide or N-methylpyrrolidone.

4. The process of claim 1, wherein the reaction is conducted at a temperature from 95° to 150° C.

5. The process of claim 1, wherein from 1 to 1.5 mol of the amine of formula (III) is reacted per mol of phenylurea of formula (II).

6. The process of claim 5, wherein the molar amount of amine of formula (III) ranges from 1 to 1.2 mol.

* * * * *